United States Patent [19]

Hahn et al.

[11] 4,274,413
[45] Jun. 23, 1981

[54] DEPILATORY TWEEZER

[76] Inventors: Robert H. Hahn; Neva N. Hahn, both of 333 Pembroke Mews, Toronto, Canada, M5A 2N6; Noah Salzman, 7461 Kingsley Rd., Cote St. Luc, Canada, H4W 1P4

[21] Appl. No.: 965,672

[22] Filed: Dec. 1, 1978

[30] Foreign Application Priority Data

Oct. 6, 1978 [CA] Canada .................................. 312902

[51] Int. Cl.³ .............................................. A61B 17/41
[52] U.S. Cl. ............................ 128/303.13; 128/303.17
[58] Field of Search ...................... 128/303.13, 303.14, 128/303.17, 354; 219/223, 233, 234

[56] References Cited

U.S. PATENT DOCUMENTS

| 2,012,937 | 9/1935 | Bevoy | 128/303.14 X |
| 3,100,489 | 8/1963 | Bagley | 128/303.17 |
| 3,614,382 | 10/1971 | Politzer | 128/303.14 X |
| 3,911,241 | 10/1975 | Jarrard | 128/303.14 X |
| 3,934,115 | 1/1976 | Peterson | 128/303.14 X |
| 4,033,350 | 7/1977 | Hoshi | 128/303.13 |
| 4,041,952 | 8/1977 | Morrison, Jr. et al. | 128/303.13 |
| 4,174,713 | 11/1979 | Mehl | 128/303.13 |
| 4,174,714 | 11/1979 | Mehl | 128/303.13 |

FOREIGN PATENT DOCUMENTS 2315286  1/1977  France ................................ 128/303.17

Primary Examiner—Lee S. Cohen
Attorney, Agent, or Firm—Alan H. Levine

[57] ABSTRACT

A tweezer mechanism having a pair of electrodes for automatically applying high frequency energy to a hair, upon the hair being gripped precisely in its proper place by the apparatus. The tweezer is comprised of a pair of elongated arms resiliently biased away from each other, the arms having sections adjacent their ends parallel to each other at their closest adjacency, the sections having electrically conductive surfaces for contacting opposite sides of and confining a hair, and an electrical switch operated when the location of the arms is a predetermined distance apart no smaller than the distance between the conductive surfaces being the thickness of a hair. In one embodiment the electrodes are spaced a precise distance from the skin to safeguard against burning and to allow maximum safe energy to be applied, whereby reliable coagulation of the root can occur.

20 Claims, 3 Drawing Figures

DEPILATORY TWEEZER

BACKGROUND OF THE INVENTION

This invention relates to a novel apparatus used during the removal of hair, and more particularly to a novel tweezer used during the hair removal process involving high frequency coagulation of the hair root.

There are two general methods of hair removal by high frequency coagulation of the root of the hair. The first is to insert a needle into the hair follicle, following which the needle is energized by a high frequency electrical current. This current coagulates the root of the hair, after which the hair can be plucked from the follicle.

However even with a skilled operator, patients are sometimes burned or cut by the needle; the insertion of the needle itself is painful, particularly in tender skin areas. Further, only one hair at a time can be treated and removed. Accordingly the removal of hair, particularly where large areas of hair are to be removed, is a sometimes painful, uncomfortable, and tedious process.

The second method utilizes a tweezer to grip the hair on opposite sides by a pair of spaced electrodes at a point spaced from the skin. A high frequency current is applied to the electrodes, and the current flows along the hair to the root of the hair, thereby coagulating the root, after which the hair can be removed.

The difficulty with the latter method is that even in the hands of a skilled operator, there is danger of the electrode touching the skin, which would cause burns and sometimes scarring. If the electrodes are too close to the skin, they can cause a burn, and if not close enough, the epilation process will not be complete since the hair is not a good conductor of high frequency energy and the path length for the energy is too great. Thus after the hair is removed another will grow again, since the root will not have been coagulated.

Further, as in the former method, only one hair at a time can be removed, which results in a tedious and time consuming (and therefor expensive) method for removing hair, even from a small skin area.

In the latter method after the electrodes are applied to the hair, a separate foot-operated switch must be used to switch on the high frequency energy. The operator must be very skilled to estimate when the electrodes are in proper positions, with a proper amount of pressure on the hair, and co-ordinate operation of the foot-operated switch. Should the electrodes be applied to a great many hairs in sequence, it is highly likely that current would sometimes by applied before the electrodes are properly in place, or with excess compression of individual ones of the hair resulting in either improper coagulation of the root, burning of the skin, touching of the electrodes together causing a short circuit of the electrodes, etc.

An apparatus of the kind to utilize the latter method is sold by Depilatron Inc., Woodbridge, Conn., U.S.A., under the Trade Mark "Depilatron", Model DP-206.

SUMMARY OF THE INVENTION

The present invention, however, is a tweezer mechanism having a pair of electrodes for automatically applying high frequency energy to a hair, upon the hair being gripped precisely in its proper place by the apparatus. Since the high frequency current is applied at the correct electrode pressure across the hair, there is no danger of the electrodes short circuiting.

Further, the electrodes are imbedded in or disposed on the surface of a pair of arms, preferably with a ridge or rim of insulating material around them. Accordingly the electrodes cannot touch the skin, and current, which is preferably applied automatically by means to be described below, is safely insulated from the skin, effectively reducing or eliminating the possibility of burning.

In another embodiment, insulative spacers separate the electrodes by the thickness of a hair, thereby precisely spacing the electrodes when current is applied, without excess pressure being applied to the hair.

In a further embodiment, the front edge of one electrode is broadened and an insulative comb extends forward thereof, for guiding a plurality of hairs to a region between a pair of broad electrodes. The electrodes are spaced as in the aforenoted embodiment by an insulative spacer from the skin. With this embodiment, a large number of hairs can be treated at the same time.

Accordingly during epilation of hair, burning of the skin is substantially eliminated, both due to the spacing of the electrodes from the skin by the insulative spacer and due to the automatic switching on of the current. Since a large number of hairs can be treated at the same time, the tedium and expense of treatment is reduced.

Since the location of the electrodes is precisely controlled with an arm or the arms touching the skin, high frequency energy can be applied to the maximum intensity allowed under safe operating conditions. This ensures that coagulation of the root will take place with certainty, thus increasing the reliability of permanence of the hair removal.

In general the invention is a depilatory tweezer comprising means for retaining a hair between a pair of electrodes, which includes a pair of elongated arms resiliently biased away from each other, the arms having facing sections adjacent their ends parallel to each other at their closest adjacency, the sections having electrically conductive surfaces, and the insulative spacers extending outwardly from one of the surfaces toward the other and extending only as far in height and in length as to allow retention of a hair between and in contact with the electrically conductive surfaces when the arms are in closest adjacency, without interference by the insulative spacer means.

In a preferred embodiment, the inventive depilatory tweezer comprising means for retaining hair between a pair of electrodes includes a pair of elongated arms resiliently biased away from each other, the arms having sections adjacent their ends parallel to each other at their closest adjacency, the sections having electrically conductive surfaces for contacting opposite sides of and confining a hair, and the electrical switch means operated when the location of the arms is a predetermined distance apart no smaller than the distance between the conductive surfaces being the thickness of a hair.

The invention is also a depilatory tweezer comprising means for retaining a plurality of hairs between a pair of electrodes comprising a pair of elongated insulative arms resiliently biased away from each other, one disposed above the other, the lower of the arms having a sharp wedge-shaped front edge; a first conductive electrode forming the upper surface of the lower of the arms a predetermined distance from the front edge; a second conductive electrode forming at least part of the lower surface of the upper of the arms opposite the first conductive electrode, said first and second electrodes being parallel to each other on closest adjacency thereof; the ends of said arms and said electrodes being substantially wider than the remainder of said arms; and an insulative comb structure extending forward from the front edge of the lower of said arms adapted to gather and retain hairs between the tines of the comb structure as the lower arm is moved forward over a hairy surface.

In another embodiment, the inventive depilatory tweezer comprising means for retaining a plurality of hairs between a pair of electrodes is comprised of a pair of elongated insulative arms resiliently biased away from each other, one disposed above the other, the lower of the arms having a sharp wedge-shaped front edge; a first conductive electrode forming the upper surface of the lower of the arms a predetermined distance from the front edge; a second conductive electrode forming the lower surface of the upper of the arms opposite the first conductive electrode, said first and second electrodes being parallel to each other on closest adjacency thereof; the ends of said arms and said electrodes being substantially wider than the remainder of said arms; an insulative comb structure extending forward from the front edge of the lower of said arms adapted to gather and retain hairs between the tines of the comb structure as the lower arm is moved forward over a hairy surface and, electrical switch means operated when the location of said arms is a predetermined distance apart in which the electrodes are a distance apart no smaller than the thickness of a hair.

The invention further is a method of operating a depilatory tweezer comprising touching opposite sides of a hair with a pair of electrodes extending from a pair of insulating handles, and operating a switch by the action of one handle moving toward the other during or just prior to the touching of the hair.

A better understanding of the invention will be obtained by reference to the detailed description below, and to the following drawings, in which.

Figure 1:
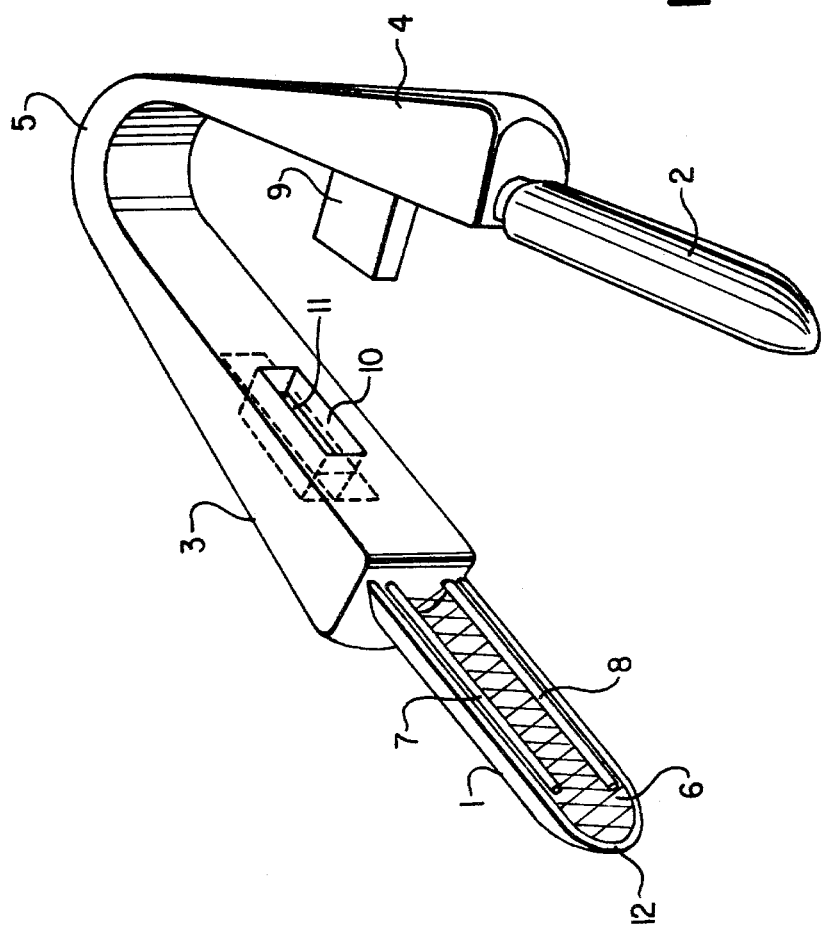
FIG. 1 is a perspective view of one embodiment of the invention.

Turning to FIG. 1, the tweezer is comprised of a pair of arms 1 and 2 which extend from the ends of handles 3 and 4. The handles are joined at their ends 5 remote from arms 1 and 2. Preferably handles 3 and 4 are fabricated out of a single molding of plastic, whereby they may be resilient biased away from each other.

Alternatively two separate handles may be pinned and spring biased, for example. An electrode 6 is located at the surface of arm 1, facing a similar electrode on the adjacent surface of arm 2. Spacers 7 and 8, formed of elongated insulative ridges along the top and bottom edges of electrode 6 are about the thickness of a hair, whereby, when the arms 1 and 2 are brought together, they form a barrier prohibiting the electrodes from short circuiting.

The insulative ridges 7 and 8 do not extend as far as the end of the electrode, to accommodate the contacting of a hair by both the the opposing electrodes, without interference by the insulative ridges. Alternatively only a single ridge may be used, or one or more tiny mesa-like protrusions, etc., as the spacer. A suitable material for the ridge is silicone rubber, or an adhesive plastic strip.

A protrusion 9 extends from the inward side of handle 4 toward the inward side of handle 3. A switch means is located, preferably embedded in handle 3, so that it can be operated by protrusion 9.

Preferably a slot 10 of similar cross-section as protrusion 9, but slightly larger, shown partly in dotted outline is provided within handle 3 to accommodate the incursion of protrusion 9.

As one embodiment of the switch, a resilient conductive strip 11 shown in dotted outline, which may be a spring or other yieldable material, is held within slot 10. Upon protrusion 9 entering slot 10, it pushes against resilient conductor 11, causing it to make contact with an electrical terminal (not visible) behind it. A switch is thereby formed which is operated by protrusion 9.

Preferably electrode 6 is spaced from the edge of arm 1 by an insulative edge 12 of arm 1. The electrode structure within arm 2 is similar to that of arm 1.

The electrode can be either a deposit of conductive material on the surface of the plastic arm, or a foil or strip inlaid within or adherent to the surface, or can be a flat surfaced rod embedded in, or surrounded by a plastic sheath over its rear and side surfaces. The conductive material can be brass, nickel plated steel, etc.

In operation, the end of the tweezer arms are brought to the surface of the skin and a hair enters the region between the end of the arms and insulative ridges 7 and 8. The tweezer is then closed, thereby causing electrode 6 and the corresponding one of arm 2 to touch the hair on opposite sides thereof. Insulative ridges 7 and 8 space the arms precisely, and stop the arms from squeezing the hair too tightly, and also stop the electrodes from short circuiting.

As the arms are brought closer together by an operator pinching handles 3 and 4 together, protrusion 9 enters slot 10, causing operation of the switch. Preferably the location of the switch and the length of protrusion 9 are set such that the switch operates just as the opposite sides of the hair come into contact with the electrodes.

The switch, of course, should be connected to the operation circuitry of a radio frequency (i.e. 27 megaherz) signal generator which typically has an output power of about 3 watts. The output terminals of the signal generator are connected to electrode 6 and the corresponding electrode in arm 2. Therefore it may be seen that exactly at the correct instant, when the hair is in proper location between the electrodes, the radio freqency energy is turned on and is applied to the hair.

Due to the presence of the insulative edge 12 around electrode 6 (with similar construction in arm 2), the tweezer can grasp the hair while the arms 1 and 2 are touching the skin of a patient, without fear that the electrodes would be in contact therewith. Burning of the skin is thus avoided since the electrode current does not come into direct contact therewith. Furthermore, the insulative edge 12 spaces the electrodes an optimum distance from the skin, thereby allowing the application of radio frequency energy at the optimum position with respect to the route. Maximum safe energy can thus be used.

Accordingly, even a relatively unskilled operator can accurately operate the depilatory tweezer without fear of burning the skin of patients, and without fear of applying the radio frequency energy at the wrong time, or to short circuited electrodes.

Figure 2:
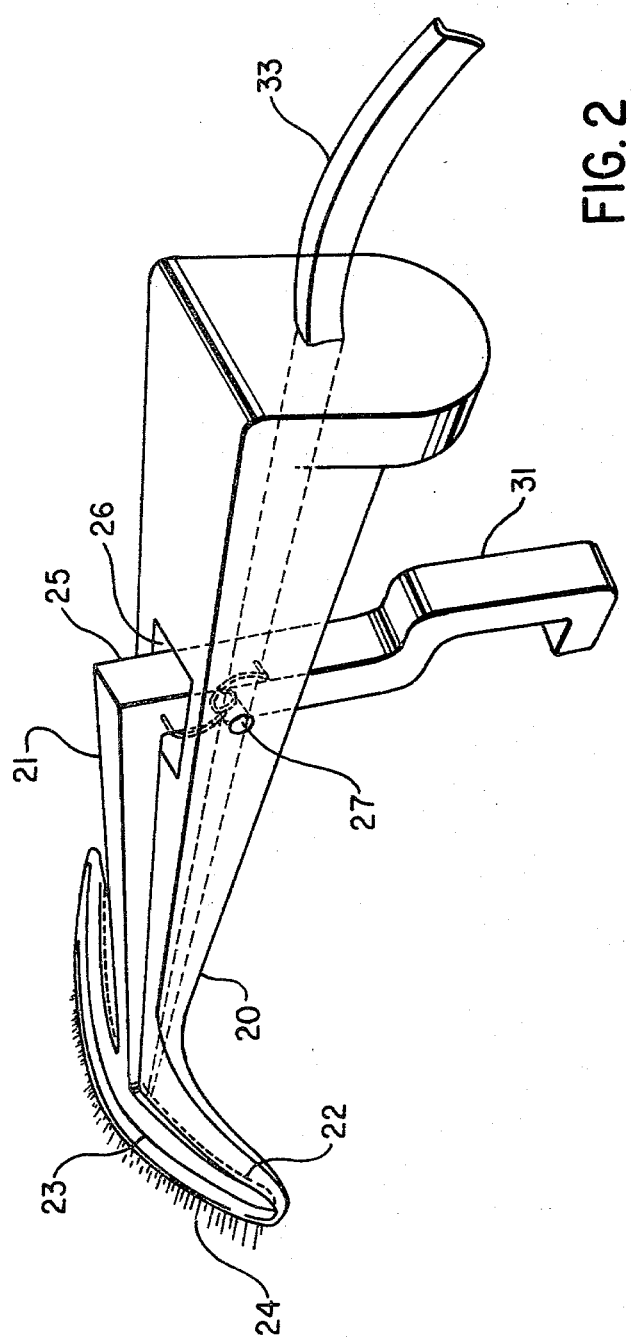
FIG. 2 is a perspective view of a second embodiment of the invention.
Figure 3:
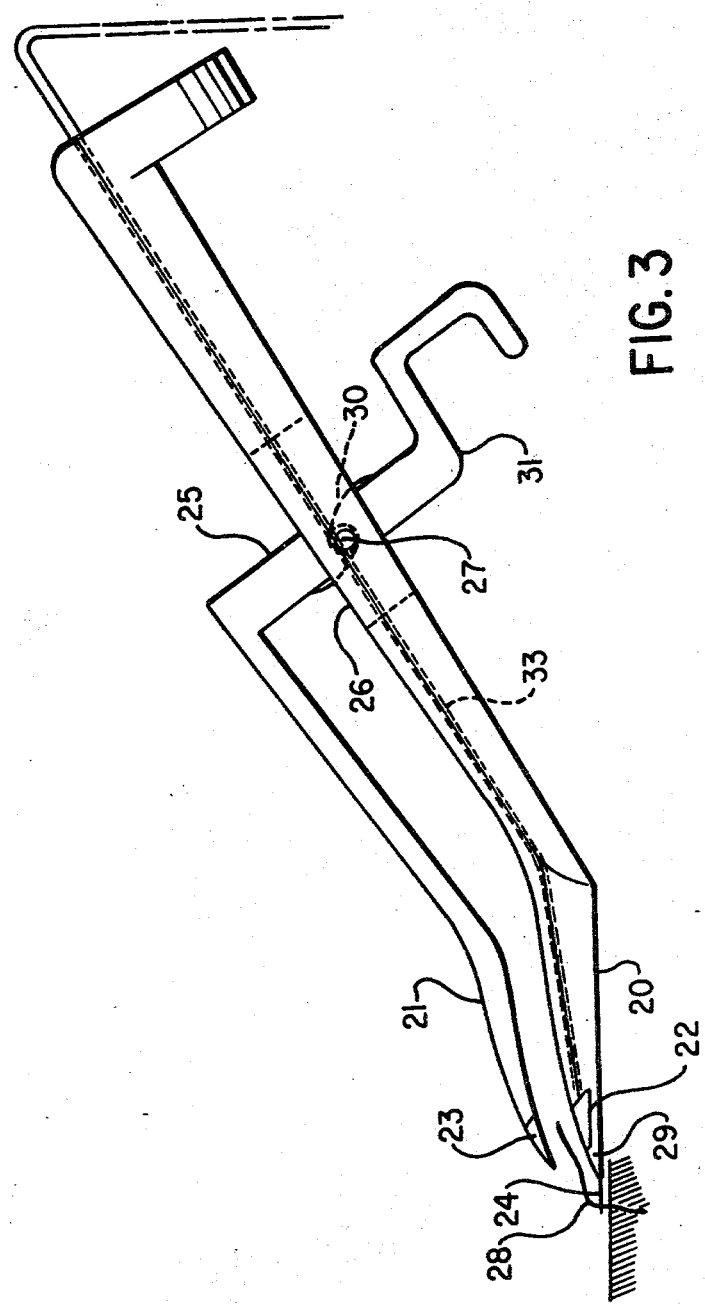
FIG. 3 is a side elevation of the second embodiment of the invention.

Turning now to FIGS. 2 and 3, another embodiment of the invention is shown. A pair of arms 20 and 21 are located one above the other. A first electrode 22 is embedded a predetermined distance from the end of electrode 22 and the end of electrode 23 are parallel to each other, so that the electrodes may be in contact along a broad surface when they are placed together.

The end of arm 20 is wedge shaped, having a sharply acute angle.

The ends of both arms 22 and 23 are widened broadly and the electrodes 22 and 23 extend virtually from one side to the other. Indeed, the entire front surface from side to side of the end of widened arm 21 maybe formed of conductive material.

Preferably an insulative comb structure 24 extends forward of the front edge of the lower arm 20 across its entire front. The bottom of the forward portion of arm 20 is preferably flat and coextending with the comb structure 24, whereby it may be placed close to the skin.

A crossmember 25 extends through a hole 26 in lower arm 20, and is attached at its upper end to the end of arm 21. Crossmember 25 is rotatably pinned by pin 27 through hole 26 to the inner sides of the hole in arm 20, and is resiliently biased by spring 30 clockwise with respect to arm 20. The bottom of crossmember 25 is formed to a finger handle 31 or the like by which counterclockwise pressure can be exerted on crossmember 25.

In operation, the bottom surface of arm 20 is placed in contact with the hairy surface of the skin, and is pushed forward. Comb 24 gathers hairs 28 between its tines, and holds them in place while it falls over the surface of electrode 22. A wedge of insulative material 29 of the lower arm 20 forms a guard whereby electrode 22 is prohibited from touching the skin; it also spaces electrode 22 precisely from the skin, similar to insulative edge 12 of FIG. 1.

Once a sufficient number of hairs fall over electrode 22, pressure is exerted on handle 31 which causes arm 21 to move downwardly toward arm 20. Electrode 23 therefore pushes the hairs 28 toward electrode 22, enclosing them therebetween. Radio frequency energy is then applied by means of wires 33 (shown partly in dashed outline) to electrodes 22 and 23, which allows it to flow over the contacted two sides of each hair via their roots thereby coagulating them. The tweezer thereafter is lifted, pulling the hairs out of their follicles, while pressure is maintained by means of compression of the handle 27.

After entire apparatus is lifted from the skin, pressure on handle 31 is released. The hair between the electrodes is discarded, and the tweezer is operated again as described above.

The present embodiment also can accommodate spacers as described with reference to the embodiment of FIG. 1 but of different form. A small number of solid cylindrical mesas may be located at two or three placed on the upper surface of the bottom arm 20 or the lower surface of the upper arm 21, adjacent electrodes 22 and 23. This structure spaces the electrodes apart approximately the thickness of a hair at their closest adjacency. Since upon applying pressure on handle 31 the hair is not squeezed, removal of the hair once the roots are coagulated is effected by means of comb 24, rather than pressure between electrodes 22 and 23.

The present embodiment, with or without the spacers also preferably also accommodates a switch similar to that described with reference to the embodiment of FIG. 1. Accordingly when the upper electrodes 23 moves into proper location with respect to electrode 22, radio frequency energy is automatically applied across all of the hairs by electrodes 22 and 23.

It may be seen that the last-described embodiment ca be used to treat a large number of hairs at the same time. yet the danger of radio frequency energy burns is avoided due to the precise spacing of the electrodes away from the skin, while the energy is applied when the tweezer holds the hair precisely whereby radio frequency energy is applied most efficiently.

While the above description has been concerned with a number of preferred embodiments, numerous variations or other embodiments may now become evident to a person skilled in the art understanding this invention. All such variations and embodiments are considered as encompassed by the present invention, as defined in the claims appended hereto.

I claim:

1. A depilatory tweezer comprising means for retaining a hair between a pair of electrodes, said means including:
   (i) a pair of arms resiliently biased away from each other, each of said arms having a section adjacent its end parallel to the other at their closest adjacency,
   (ii) said sections having electrically conductive surfaces,
   (iii) insulative spacer means extending outwardly from one of said surfaces toward the other, the spacer means extending only so far as to allow retention of a hair between and in contact with the electrically conductive surfaces when the arms are in closest adjacency, without interference by the insulative spacer means, and
   (iv) means for conducting radio frequency current to said electrically conductive surfaces.

2. A depilatory tweezer as defined in claim 1, in which the insulative spacer means is comprised of at least one insulative ridge extending along a portion of at least one of said parallel sections.

3. A depilatory tweezer as defined in claim 1, in which the pair of arms extend forwardly of a pair of handles, said handles being connected at their remote end, and further including means biasing the handles away from each other.

4. A depilatory tweezer as defined in claim 1, 2 or 3, further including electrical switch means automatically operated under control of an arm when the distance between said conductive surfaces is no smaller than the thickness of a hair for controlling the application of radio frequency current to the electrically conductive surfaces.

5. A depilatory tweezer as defined in claim 1, 2 or 3, further including a protrusion extending from one of the pair of arms toward the other of the arms, means for automatically operating a switch upon the closure of said protrusion toward the other of the pair of arms for controlling the application of radio frequency current to the electrically conductive surfaces.

6. A depilatory tweezer as defined in claim 1, 2 or 3, further including a protrusion extending from one of the pair of arms toward the other of the pair of arms, a slot of similar cross-section as the protrusion in the other of the pair of arms for accommodating the protrusion; a switch within the slot, operable upon insertion of the protrusion therein and compression of the switch thereby, operation of the switch occurring at a separation of said electrically conductive surfaces no smaller than the thickness of a hair.

7. A depilatory tweezer as defined in claim 1, 2 or 3, in which the spacer means is comprised of a pair of insulative ridges extending similar distances along at least part of the inner edge of said parallel sections, and further including a protrusion extending from one of the pair of arms toward the other of the pair of arms, a slot of similar cross-section as the protrusion in the other of the pair of arms for accommodating the protrusion; a switch within the slot, operable upon insertion of the protrusion therein and compression of the switch thereby, operation of the switch occurring at a separation of said conductive surfaces no smaller than the thickness of a hair.

8. A depilatory tweezer as defined in claim 1 or 3 in which the spacer means is comprised of a pair of insulative ridges extending similar distances along at least part of the edges of said parallel sections.

9. A depilatory tweezer as defined in claim 1, in which the insulative spacer means is comprised of a protrusion extending from one of the arms toward the other.

10. A depilatory tweezer comprising means for retaining a hair between a pair of electrodes, said means including:
    (i) a pair of arms resiliently biased away from each other, said arms having sections adjacent their ends parallel to each other at their closest adjacency,
    (ii) said sections having electrically conductive surfaces for contacting opposite sides of and confining a hair,
    (iii) means for conducting radio frequency current to said conductive surfaces, and
    (iv) electrical switch means automatically operated under control of an arm when the distance between said conductive surfaces is no smaller than the thickness of a hair for controlling the application of radio frequency current to the electrically conductive surfaces.

11. A depilatory tweezer as defined in claim 1, 9 or 10, further including an insulative rim spaced between the edges of the arms and the electrically conductive surfaces.

12. A depilatory tweezer comprising means for retaining a plurality of hairs between a pair of electrodes comprising a pair of elongated insulative arms resiliently biased away from each other, one disposed below the other, the lower of the arms terminating in a sharply acute angle; a conductive electrode forming the upper surface of the lower of the arms a predetermined distance from the angle; a second conductive electrode forming the lower surface of the upper of the arms, said upper and lower surfaces being parallel to each other on closest adjacency thereof; the ends of said arms supporting said electrodes being substantially wider than the remainder of said arms; an insulative comb structure extending forward from the wider end of the lower of said arms, adapted to gather and retain hairs between the tines of the comb structure as the lower arm is moved forward over a hairy surface, and conductive means contacting the first and second electrodes respectively for conducting current thereto.

13. A depilatory tweezer as defined in claim 12, in which at least the wider portion of the lower of the arms adjacent its end has a flat bottom, the remainder of the lower of the arms being inclined upwardly therefrom.

14. A depilatory tweezer as defined in claim 13 in which at least the entire front of the widened portion of the upper arm is comprised of electrically conductive material constituting the second electrode.

15. A depilatory tweezer as defined in claim 14 in which the upper arm extends along the lower arm, and is attached to a crossmember passing through a hole in the lower arm at approximately a right angle thereto, the crossmember being rotatably pinned across and to the lower arm at a central location through the hole, and a lower extension to the crossmember shaped to accommodate the finger of an operator for moving the crossmember about the point of pinning, thereby bringing the conductive electrode at the front of the upper arm into adjacency with the conductive electrode at the surface of the lower arm.

16. A depilatory tweezer as defined in claim 12, 13 or 15 further including electrical switch means connected in series with a circuit for controlling the application of current to the electrodes operated as a result of the location of said arms when the conductive surfaces are a predetermined distance apart no smaller than the thickness of a hair.

17. A depilatory tweezer as defined in claim 15, including an insulative spacer means extending from one of said arms toward the other adjacent said electrodes, the spacer means being the thickness of a hair, the spacer means extending only so far as to allow retention of hair between and in contact with the electrically conductive surfaces when the arms are in closest adjacency without being compressed.

18. A method of operating a depilatory tweezer comprising combing a plurality of hairs so that the hairs fall over a first electrode associated with a first handle of the tweezer, moving a second electrode associated with a second handle of the tweezer over the hairs into adjacency to but without touching the first electrode whereby two sides of the hairs are brought into electrical contact with respective ones of the electrodes, and applying radio frequency energy to the electrodes by closing a switch connected in a circuit for applying current to the electrodes.

19. A method as defined in claim 18, in which the tweezer includes a pair of arms and the radio frequency energy is applied under control of a switch which is operated by the action of said arms moving toward each other during or just prior to the touching of the hairs.

20. A method of operating a depilatory tweezer as defined in claim 18 or 19, including bringing the tweezer adjacent the skin of a patient, and interposing an insulator of predetermined width as part of the tweezer between said first electrode and the skin.

* * * * *